United States Patent [19]

Holewinski et al.

[11] Patent Number: 4,708,650
[45] Date of Patent: Nov. 24, 1987

[54] DIRECT DELIVERY SYSTEM FOR DENTAL MATERIALS

[75] Inventors: Robert D. Holewinski, Lakehurst; William J. Blatherwick, Hamilton Square; Leslie Hamilton, Trenton, all of N.J.; Thomas E. Wells, Sr., Richboro, Pa.

[73] Assignee: Johnson & Johnson Dental Products Company, East Windsor, N.J.

[21] Appl. No.: 827,686

[22] Filed: Feb. 10, 1986

[51] Int. Cl.$^4$ .............................................. A61C 5/04
[52] U.S. Cl. ..................................................... 433/90
[58] Field of Search ............................. 433/90, 80, 89; 222/386

[56] References Cited

U.S. PATENT DOCUMENTS 3,221,409 12/1965 Thiel et al. .............................. 433/90
4,472,141 9/1984 Dragan .................................. 433/90

Primary Examiner—Robert Peshock
Attorney, Agent, or Firm—Donal B. Tobin

[57] ABSTRACT

An applicator for accurately dispensing small amounts of fluids to tooth surfaces, including a handle, a nozzle which includes a reservoir for fluid and a piston member, and a lever, spring, plunger member, whereby activation of the lever forces the plunger against the piston which, in turn, forces fluid out of the reservoir through the nozzle.

6 Claims, 10 Drawing Figures

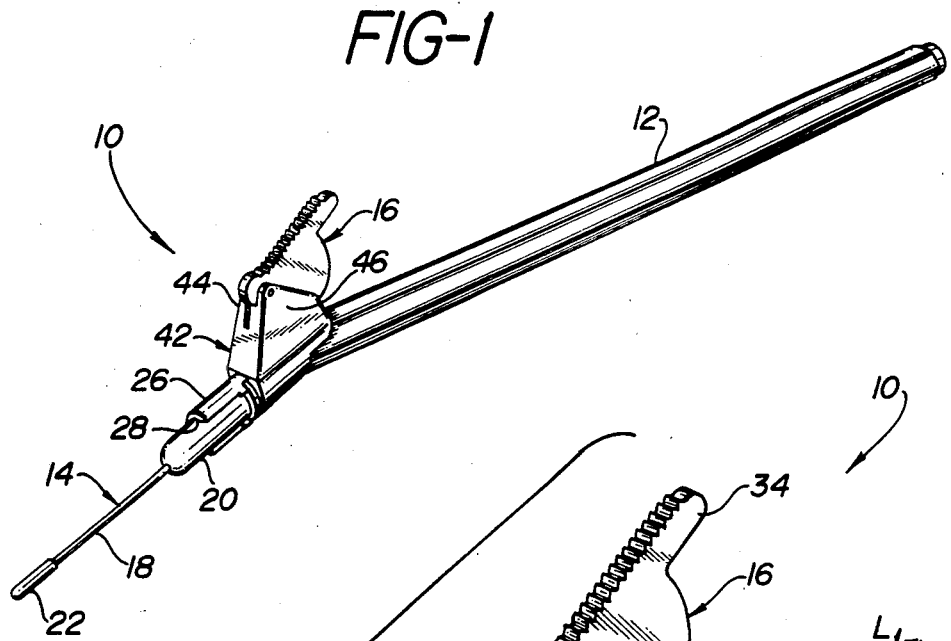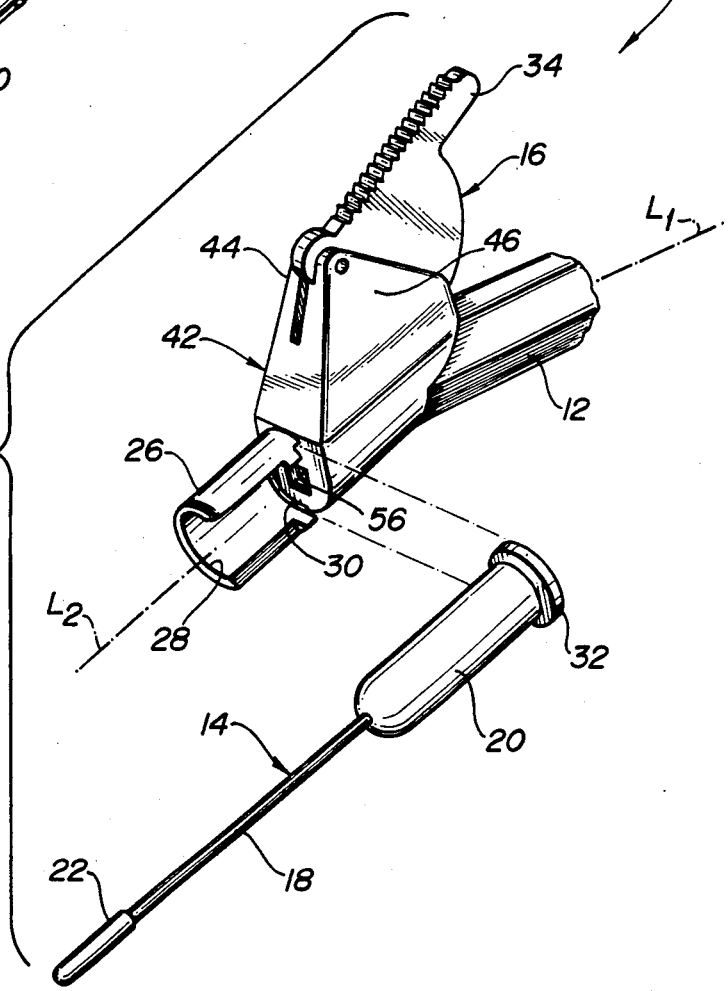

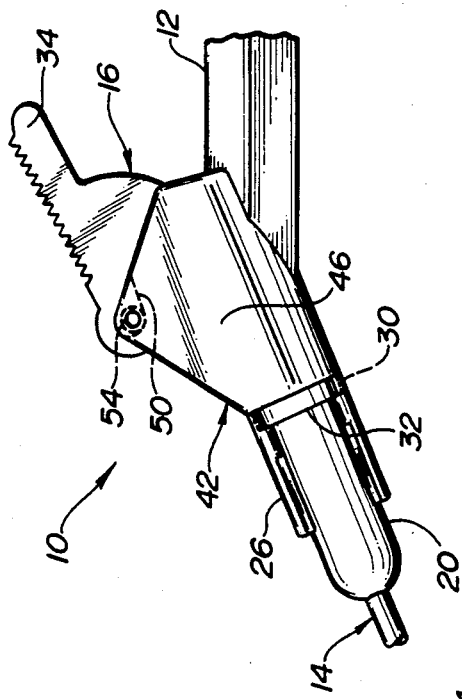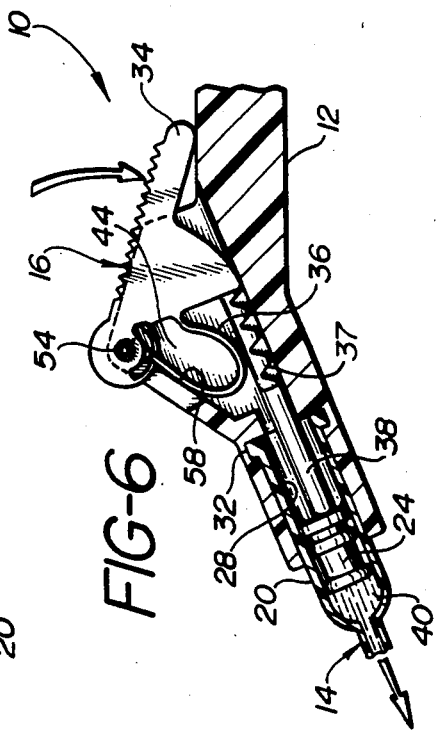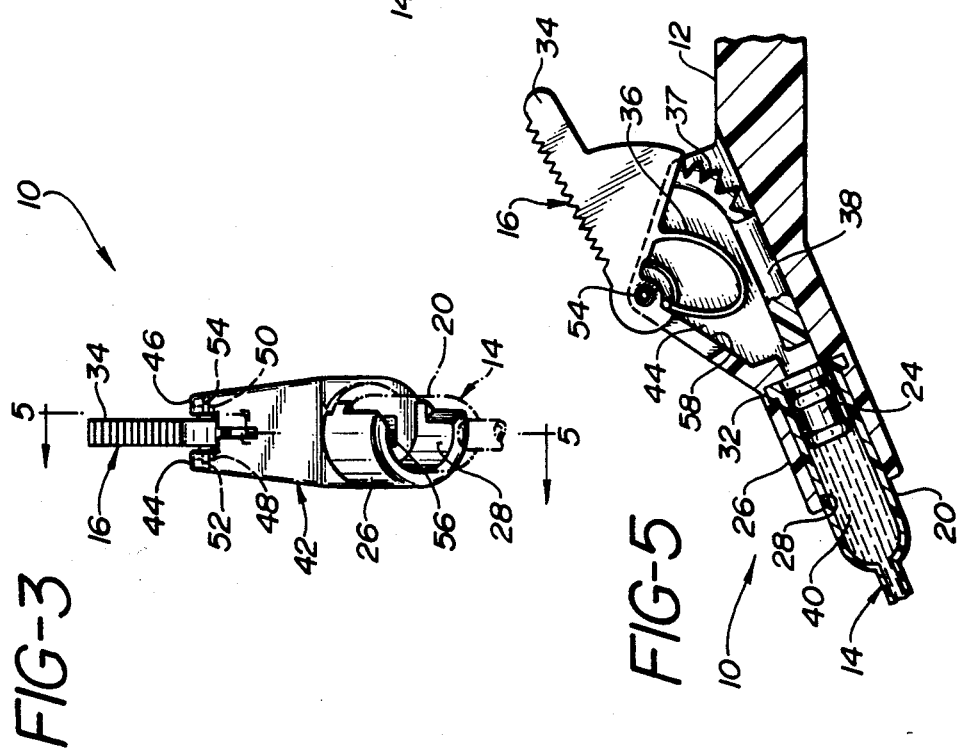

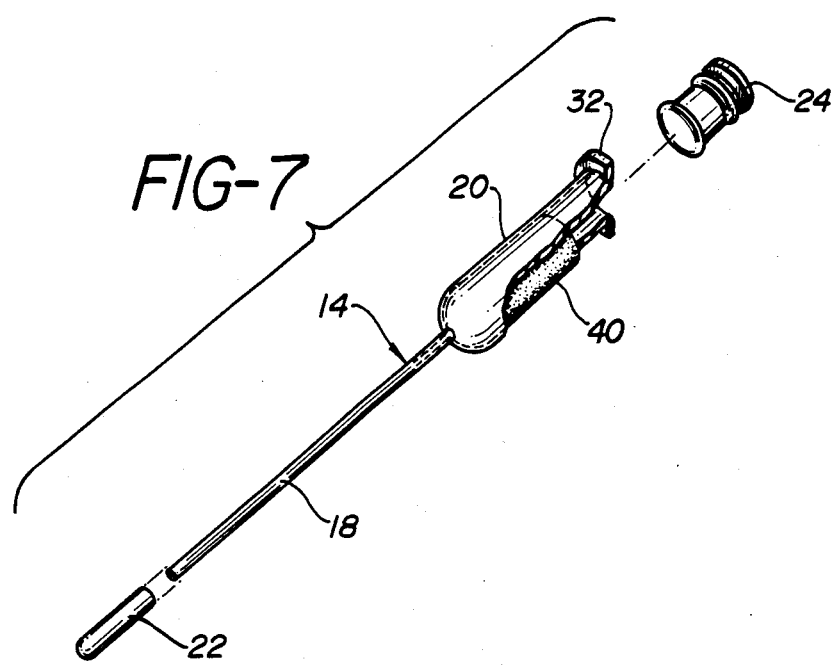
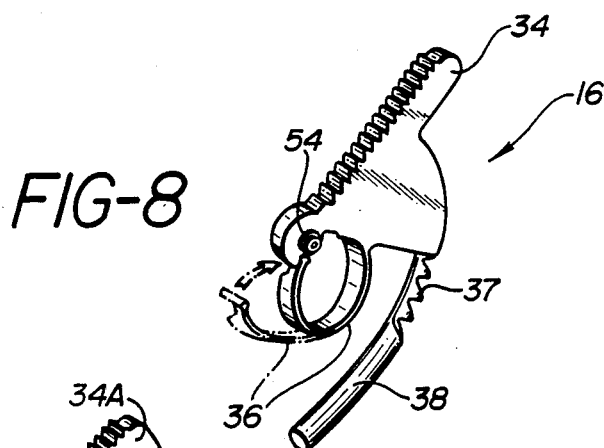
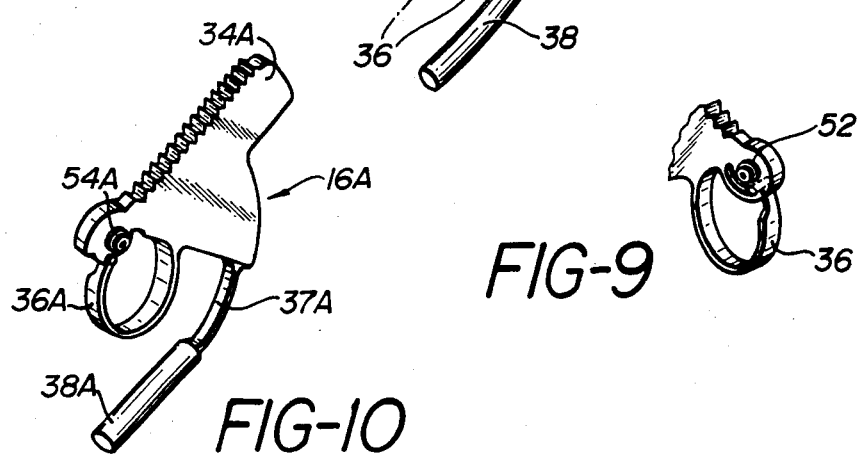

DIRECT DELIVERY SYSTEM FOR DENTAL MATERIALS

This invention relates to an applicator for accurately dispensing small amounts of a fluid to the surfaces of teeth.

BACKGROUND OF THE INVENTION

For some years now, there has been an increasing interest in treating teeth with fluid polymerizable monomers which are activated to form polymers either on the surface of teeth or in cavities. Initially, it was the practice to apply such polymerizable monomers with a brush or spatula to the tooth surface. Such treatment was awkward in that it was difficult to control precisely the amount and exact position of application. There has more recently been considerable work done in applicators with nozzle tips for applying predetermined amounts of polymerizable fluid to the teeth. For instance, reference is made to Dragan, U.S. Pat. No. 3,581,399, who discloses a system that is particularly designed for the application of filled resin systems useful as restorative composites, and to Perfect, U.S. Pat. No. 4,043,042, who discloses an applicator that is designed specifically for applying pit and fissure sealant to the surfaces of teeth to prevent the formation of caries.

This invention is directed to an applicator for accurately dispensing small amounts of fluids, such as pit and fissure sealants, acid etching fluids, fluoride treatment fluids, or filled systems such as dental composites. The applicator of this invention is relatively inexpensive to manufacture, is simple to operate, and applies with precision a predetermined amount of fluid directly to the desired site on the tooth.

SUMMARY OF THE INVENTION

The applicator provided by this invention comprises, in combination:
(a) an elongated handle member having a first longitudinal axis and a front end;
(b) nozzle receiving means located at the front end of said handle member, said nozzle receiving means including a first housing having a second longitudinal axis that is oriented at a slight angle downwardly from said first longitudinal axis, said first housing having a front end, a rear end, a longitudinally extending cut-out portion that extends to the front end of said first housing, and a plunger access port located at the rear end of said first housing, wherein said plunger access port communicates to a second housing that extends upwardly from said handle member;
(c) nozzle means arranged and constructed to contain a predetermined amount of fluid, said nozzle means including a front discharge tip and a rear portion comprising a tubular body portion defining a reservoir for said fluid, said tubular body portion including an open end at the rear thereof and a piston member therein;
(d) said nozzle means inserted in said cut-out portion so that said discharge tip extends beyond the front of said first housing in a direction approximately coincident with said second longitudinal axis, at least the portion of said tubular portion that includes the said open end being contained within said first housing;
(e) plunger means mounted such that it can reciprocate through said access port in a direction approximately coincident with said second longitudinal axis from a retracted position to an activated position such that when the plunger is in the activated position it engages said piston member contained in said tubular body portion;
(f) said plunger means being attached by a flexible connector to finger operable lever means pivotally mounted in said second housing such that when said lever means is depressed the plunger means is pushed from the retracted to the activated position;
(g) spring means in said second housing operatively connected to said lever means to normally maintain the plunger means in the retracted position, whereby when the lever means is depressed to move the plunger means to the activated position, the plunger means engages the piston means and moves it in a direction approximately coincident with said second longitudinal axis which thereby forces fluid contained in said nozzle means out of the nozzle means through the front discharge portion.

THE PRIOR ART

Dragan, in U.S. Pat. No. 3,581,399, discloses a composite resin filling syringe which includes a syringe and a nozzle tip that can be prefilled with a predetermined amount of resin to be delivered through the tip of the nozzle.

Perfect, in U.S. Pat. No. 4,043,042, discloses an applicator that is specifically designed for the application of tooth sealant resin systems, which applicator employs an internal chamber that is activated by a plunger that impinges against a reservoir that is described by a resilient diaphragm. Pressure on the diaphragm forces liquid contained in the reservoir out through a nozzle tip.

Morris, in U.S. Pat. No. 384,863, discloses a dental tool for delivering dental amalgam. The tool includes a handle having a cup to receive amalgam, an operating lever, and a plunger for forcing the amalgam from the cup into the cavity in the tooth.

Other prior art that shows various dental applicator tools include the following patents:

Kelly, U.S. Pat. No. 742,446, Cocherell; U.S. Pat. No. Des. 204,267; Ivory, U.S. Pat. No. 2,679,102, Katz; U.S. Pat. No. Des. 196,505; Vadas et al., U.S. Pat. Nos. 4,340,367 and 4,377,380; Dougherty, U.S. Pat. No. 4,391,590; Dougherty et al., U.S. Pat. No. 4,330,280; Welsh, U.S. Pat. No. 4,384,853; and Rudler U.S. Pat. No. 4,295,828.

A disadvantage of the devices described in most of the enumerated patents is that the activating mechanisms are relatively complicated and, hence, expensive. Typically, there is a syringe member which is activated through the entire handle member. The present invention has the advantage of being quite simple to manufacture and, therefore, is inexpensive while it is at the same time quite effective in performing the task for which it was designed.

BRIEF DESCRIPTION OF THE DRAWINGS

FIG. 1 is a perspective view of a device embodying the principles of the invention;

FIG. 2 is an exploded perspective view of the front end of the device shown in FIG. 1 with the nozzle shown oriented for insertion;

FIG. 3 is a front elevational view of the handle with the nozzle shown in phantom;

FIG. 4 is a right side elevational view of the device shown in FIG. 1 with the handle partially broken away;

FIG. 5 is a cross-sectional view taken along line 5—5 of FIG. 3, showing specifically the nozzle, the nozzle receiving chamber, the housing which encloses the plunger when it is in the retracted position and the spring and lever, with the plunger shown in the retracted position;

FIG. 6 is a cross-sectional view similar to FIG. 5 with the plunger shown in the activated positions;

FIG. 7 is a perspective view of the nozzle assembly, partially in section, showing the filler material, and showing the piston and end cap exploder;

FIG. 8 is a perspective view of the lever, spring and plunger, with the spring shown also in phantom to illustrate how the piece is molded;

FIG. 9 is a partial perspective view of the lever, spring and plunger shown on the opposite side from that shown in FIG. 8; and FIG. 10 is a perspective view, similar to FIG. 8, of an alternate embodiment of the lever, spring, plunger mechanism.

DETAILED DESCRIPTION OF THE INVENTION

Referring first to FIGS. 1 and 2, there is shown an applicator 10 that embodies the principles of the invention. The applicator includes an elongated handle 12, a nozzle 14, and a lever, spring, plunger mechanism 16.

The nozzle 14 includes a tip end 18, a tubular reservoir 20 for containing fluid to be applied, and a piston 24 (see FIGS. 5 and 6). It is also desirable to include a cap 22 to place over the end of the tip 18 to prevent fluid from leaking out. The nozzle 14 can be disposable, and can be pre-loaded with a predetermined quantity of fluid. The nozzle 14 can be made of an opaque material so that it will be light tight, and it can therefore be used to contain photopolymerizable fluids.

At the front end of the handle 12, there is a housing 26 that is adapted to receive the nozzle 14. The housing 26 is inclined at a slight angle downwardly from the longitudinal axis L₁ of the handle such that the longitudinal axis L₂ of the said housing 26 inclined slightly downwardly from the longitudinal axis of the handle L₁ (see FIG. 2). The housing 26 for receiving the nozzle includes a cut-out portion 28 into which the tubular reservoir portion 20 of the nozzle can be inserted, as is shown in FIGS. 1 and 2. Preferably, there is a slot 30 constructed to receive a flange 32 on the nozzle to hold the nozzle securely in place (see FIG. 2).

The lever, spring, plunger mechanism 16 includes a lever 34, a spring 36, and a plunger 38. The plunger 38 is connected to the finger-activatable lever 34 by a flexible connector 37. In operation, if the lever 34 is depressed (as by a finger) from the normally open position, shown in FIG. 5, to the fully activated position, which is shown in FIG. 6, the plunger 38 pushes the piston 24 in the reservoir 20 forward so that fluid 40 contained in the reservoir 20 is expelled forward and out through the tip 18 of the nozzle 14. When pressure on the lever 34 is released the spring 36 forces the lever 34 back to the retracted position shown in FIG. 5. The spring 36 is enabled to do so by the following means:

The lever, spring, plunger mechanism 16 is mounted on the applicator 10 in an upstanding housing 42 that is located at the front end of the applicator 10. The upstanding housing 42 includes side walls 44, 46 that have, at their tops, depressions 48, 50 to receive the pivot projections 52, 54 of the lever, spring, plunger mechanism 16. As shown in FIGS. 5 and 6, housing 42 is hollowed out to receive lever, spring and plunger mechanism 16. The hollowed out portion of housing 42 includes a channel surface 70 which smoothly merges into plunger access port 56 so that plunger 38 may slide smoothly along channel surface 70 into plunger access port 56. Thus, when the lever 34 is depressed, the entire mechanism 16 pivots around the pivot projections 52, 54 and thereby forces the plunger 38 through an access port 56 (see FIG. 2) between the upstanding housing 42 and the nozzle receiver housing 26 to thereby engage the piston 24 that is located in the reservoir 20 of the nozzle 14. When pressure on the lever 24 is released, the spring 36, which had been compressed against a wall 58 in the upstanding housing 42, then forces the entire mechanism 16 back into the retracted position.

In an alternative embodiment of the lever, spring, plunger mechanism (shown in FIG. 10), the flexible connector 37a can be a smooth rod rather than a serrated member, as was shown in FIGS. 5, 6, and 8.

The device of the invention is convenient because a dentist can operate the lever 34 with the finger of the hand that is holding the applicator. Fluids can be dispensed accurately, in small doses, in all directions (i.e., upwardly as well as downwardly.)

The device of the invention can be made of plastic materials. For instance, the handle 12 can be made of ABS rubber, the nozzle 14 can be made of high density polyethylene, the lever, spring, plunger mechanism 16 can be made of polyacetal resin, the piston 24, can be made of rubber, and the cap 22 can be made of polyvinyl chloride. An advantage in making the nozzle 14 of high density polyethylene is that the tip 18 can be bent and it will maintain the bent shape. This is useful in applying fluid to hard-to-reach areas.

What is claimed is:

1. An applicator for accurately dispensing a small amount of a fluid to tooth surfaces, which comprises, in combination:
   (a) an elongated handle member having a longitudinal axis and a front end;
   (b) nozzle receiving means located at the front end of said handle member, said nozzle receiving means including a first housing, said first housing having a front end, a rear end, a longitudinally extending cut-out portion that extends to the front end of said first housing, and a plunger access port located at the rear end of said first housing and having a peripheral surface, wherein said plunger access port communicates to a second housing that extends upwardly from said handle member;
   (e) plunger means mounted such that it can reciprocate through said access port from a retracted position to an activated position;
   said second housing having a plunger channel having a surface which merges smoothly with at least a portion of said plunger access port peripheral surface to permit said plunger to move smoothly through said access port;
   (f) said plunger means being integrally attached by an integral flexible connector to an integral finger operable lever means pivotally mounted in said second housing such that when said lever means is depressed the plunger means is pushed from the retracted to the activated position and smoothly through said plunger access port; and, (g) spring means in said second housing integrally connected to said lever means to normally maintain the plunger means in the retracted position.

2. The applicator of claim 1 further including nozzle means arranged and constructed to contain a predetermined amount of fluid, said nozzle means including a front discharge tip and a rear portion comprising a tubular body portion defining a reservoir for said fluid, said tubular body portion including an open end at the rear thereof and a piston member therein.

3. The applicator of claim 2 wherein said nozzle means is inserted in said cut-out portion so that said discharge tip extends beyond the front of said first housing, at least the portion of said tubular portion that includes the said open end being contained within said first housing.

4. An applicator for accurately dispensing a small amount of a fluid to tooth surfaces comprising:
 an elongated handle member having a longitudinal axis and a front end;
 nozzle receiving means located at the front end of said handle member, said nozzle receiving means including a first housing, said first housing having a front end, a rear end and a longitudinally extending cutout portion that extends to the front end of said first housing;
 said first housing including a plunger access port located at the rear end of first housing and having a peripheral surface;
 a second housing extending generally transversely from said handle member, said housing including two spaced apart side walls;
 said second housing including a channel surface connecting said two side walls and merging smoothly with at least a portion of said plunger access port;
 the confronting surfaces of said two side walls and said channel surface defining an opening in said housing;
 actuator means pivotably connected to said second housing and pivoting in said opening;
 said actuator means including an integral lever portion, an integral flexible connector portion connected to said lever portion and an integral plunger means connected to said flexible portion, said flexible portion biasing said plunger means against said channel surface to facilitate easy insertion of said plunger means through said plunger access port in said first housing.

5. The actuator of claim 4 further including return spring means integrally connected to said actuator, disposed in said slot and biasing said actuator so that said plunger means in biased away from said plunger access port in said housing.

6. The actuator of claim 4 further including nozzle means arranged and constructed to contain a predetermined amount of fluid, said nozzle means including a front discharge tip and a rear portion comprising a tubular body portion defining a reservoir for said fluid, said tubular body portion including an open end at the rear thereof and a piston member disposed in said open rear end of said nozzle means;
 said nozzle means adapted for removable insertion into said first housing so that said discharge tip extends beyond said first housing, at least a portion of said tubular portion that includes said open rear end being contained within said first housing and aligned with said plunger access port.

* * * * *